(12) United States Patent
Coffelt, Jr.

(10) Patent No.: US 6,206,297 B1
(45) Date of Patent: *Mar. 27, 2001

(54) APPARATUS AND METHOD FOR MANUFACTURING A GASDROP

(76) Inventor: Louis Arthur Coffelt, Jr., 5297 Martin St., Mira Loma, CA (US) 91752

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,907

(22) Filed: Jun. 26, 1999

Related U.S. Application Data (60) Provisional application No. 60/131,079, filed on Apr. 26, 1999.

(51) Int. Cl.[7] .................................................. A62C 5/02
(52) U.S. Cl. .............................. 239/10; 239/8; 604/290
(58) Field of Search ................................. 604/289, 290, 604/294, 296, 298; 239/333, 590, 10, 8; 222/333, 340, 360, 387, 390, 494

(56) References Cited

U.S. PATENT DOCUMENTS

| | | | |
|---|---|---|---|
| 1,900,201 | * | 3/1933 | Sager . |
| 4,722,459 | * | 2/1988 | Goncalves ............................ 222/135 |
| 5,163,929 | * | 11/1992 | Py ........................................ 604/298 |
| 5,358,477 | * | 10/1994 | Stroket ................................... 604/80 |
| 5,865,790 | * | 2/1999 | Bair ........................................ 604/35 |
| 5,881,956 | * | 3/1999 | Cohen et al. ........................ 239/333 |
| 5,893,515 | * | 4/1999 | Hahn et al. .............................. 239/7 |
| 5,997,518 | * | 12/1999 | Laibovitz et al. ................... 604/296 |

* cited by examiner

Primary Examiner—John G. Weiss
Assistant Examiner—David J. Cho (57) ABSTRACT

A Liquid/gas drop (Lg drop) intended to be used as an eye drop. The Lg drop has the form of a cluster of contiguous bubbles, and numerous constituent bubbles are volumetrically similar. Each constituent bubble encloses a gas. The cluster is formed of one thin continuous liquid wall. A device for manufacturing the Lg drop includes a flexible bottle used to inject a gas into a chamber, and a flexible bottle used to inject a bubble forming liquid into the chamber. The chamber has an outlet which is used to induce an accumulation of bubbles. This accumulation forms the Lg drop. A method of making the Lg drop includes manufacturing volumetrically similar bubbles, and inducing an accumulation of the bubbles. The accumulation obtains a particular total mass causing the Lg drop to fall from the device.

1 Claim, 4 Drawing Sheets

APPARATUS AND METHOD FOR MANUFACTURING A GASDROP

This appln claims the benefit of Provisional No. 60/131,079 filed Apr. 26, 1999.

BACKGROUND OF THE INVENTION

Eye drops are a well know method of administering a sterile liquid to the eye. And also well known is the conventional solid drop. Typically, a flexible plastic bottle having a dispensing tip in used to form and dispense a solid drop of liquid upon an eye. A common use of these eye drops is for redness relief or lubrication. It is also well known, solid drops are very uncomfortable to administer. The initial impact of the drop on the eye may be considered slightly painful. This is partially due to the fact that a particular mass of liquid is configured such that, a very small surface area of the drop initially contacts the eye. Said small surface area may be approximately 0.2 square millimeters. After the initial contact with the eye, this surface area increases slightly. However this increased surface area is relatively small.

Therefore an innovative configuration has been developed. The same commercially available liquid described above, may be capable of forming a discrete cluster of contiguous bubbles, which has been given a title "Liquid/gas drop (Lg drop)". A gasdrop may be comprised of a similar quantity of liquid to that of a solid drop. Therefor by having a similar total mass, and distributing that mass over a greater surface area, the force per square unit of area has been greatly reduced. By significantly reducing this force, the application of the gasdrop will feel gentle as compared to the solid drop.

It is also known that upon application of a solid drop, liquid will spread to undesired portions of the face. This creates a problem for persons wearing facial make-up, and is also a substantial waste of liquid.

Therefore the gasdrop will be greatly appreciated for the improvement of retaining a substantial quantity of the liquid on the surface of the eye. The structure of the gasdrop contributes to a relatively slow application of liquid to the eye. Thereby also contributing to the feeling of a gentle application.

A liquid depleted eye drop bottle, designed to dispense a solid drop, may dispense a small cluster of bubbles. When said bottle is considered empty, a small quantity of liquid remains in the bottle. Use of this liquid depleted bottle may simultaneously inject air and liquid into the flow channel, creating a stream of bubbles. Due to the fact that the ratio of air to liquid is not controllable, a cluster dispensed by this method, will likely be comprised of greatly inconsistent size bubbles. It is obvious this method is unreliable. Therefore this non-uniform cluster is not necessarily a gasdrop as it is unpredictable, and comprised of inconsistent size bubbles. The gasdrop reliably and consistently has a predetermined overall size comprised of bubbles having a similar size.

BRIEF SUMMARY OF THE INVENTION

The present invention, is related to the field of eye drops. The gasdrop is comprised of a small cluster of contiguous bubbles. Whereas said cluster is formed of one thin continuous liquid wall. And numerous constituent bubbles have a similar size.

It is well known, there are numerous methods of forming bubbles. However these methods do not form a cluster comprised of similar size constituent bubbles. Wherein the present invention provides a reliable method to form a consistent size gasdrop. The gasdrop is formed by simultaneously injecting a selected gas and a selected liquid, into a substantially enclosed space having an outlet. This induces a stream of contiguous bubbles to flow from said space, thereof becoming inherently attached to an exterior surface. This attachment induces an accumulation to form. And subsequently, upon obtaining a particular total mass, the accumulation will fall from said exterior surface.

BRIEF DESCRIPTION OF THE SEVERAL VIEWS OF THE DRAWING

The invention is further described by reference to the appended drawings taken in conjunction with the following description where.

DETAILED DESCRIPTION OF THE INVENTION

The present invention resides in a liquid eye drop having an innovative configuration, devices for manufacturing same and methods of making same. Whereas said configuration comprises, one thin continuous liquid wall forming collectively, a bubble enclosing therein, a plurality of volumetrically similar bubbles, each enclosing therein, a gas.

A method of making said thin wall comprises, simultaneous injection of a selected liquid, and a selected gas into a substantially enclosed space having an outlet. Said injections having particular parameters conducive to the formation of a stream of contiguous bubbles. Said stream induces an accumulation, thereby forming said plurality.

Said innovative configuration has been given a title, "gasdrop". Said may be generally described as comprised of, one thin continuous liquid wall forming collectively, a closed chamber enclosing therein, a plurality of volumetrically similar closed compartments, each enclosing therein, a gas.

Embodiments of the present invention are hereinafter described with reference to the drawings, in which identical or corresponding parts are indicated by the same reference characters or numbers through the several views.

Figure 1:
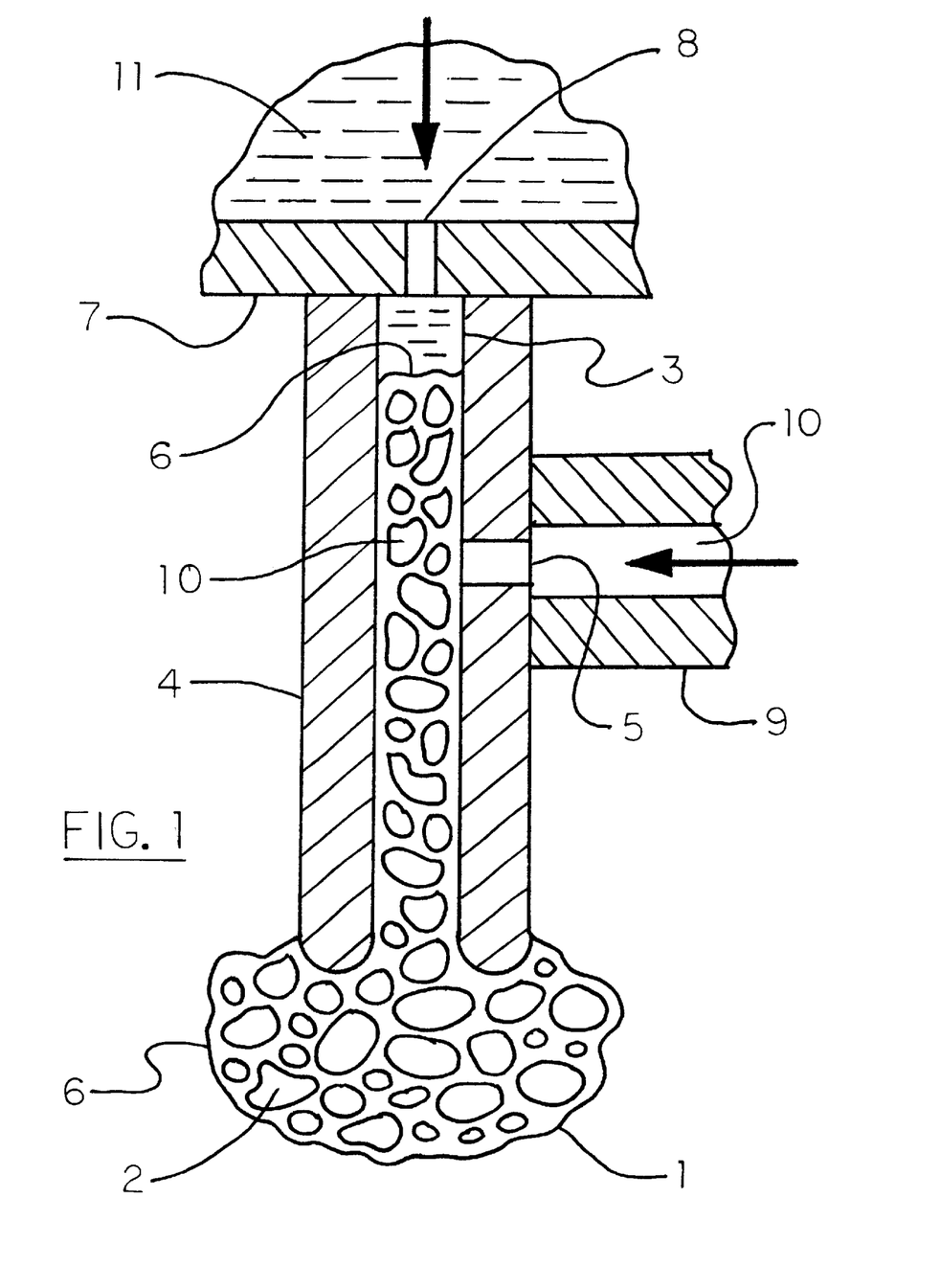
FIG. 1 is a frontal close-up sectional view of a gasdrop (1), and a dispensing tip (4).

Referring to FIG. 1, a close-up sectional view of a gasdrop (1) is shown. Said Bubble Drop is being formed by a stream of contiguous bubbles. Said stream originating within a substantially enclosed space. Each bubble (2) enclosing therein, a gas (10). Wherein said gasdrop is comprised of one thin continuous liquid wall (6).

The term "bubble" will herein refer to "a thin ball of liquid enclosing a gas or air". And said ball is not necessarily spherical. As it is known, bubbles may have various shapes. Gas (10) is preferably comprised of air, however other physiologically acceptable gases may be used. It may be found there are other uses of the Lg. drop, whereas various gases may be employed.

Said thin wall (6) is comprised of a sterile physiologically acceptable bubble forming liquid (11). Said "bubble forming" refers to the required characteristics of a liquid, enabling said liquid to form a bubble by injection of air into said liquid. Liquid (11) has said required characteristics, and is capable of forming a thin ball of liquid enclosing a gas or air.

There are several, commercially available, brands of non-pharmaceutical eye drop liquids suitable to be used as liquid (11). For example: A commercially available eye drop liquid, used for redness relief. Also commercially available, a lubricant and redness relieving liquid. Said typical eye drop liquids may be comprised of purified water, and selected active ingredients. Said active ingredients may comprise, Tetrahydrozoline Hydrochloride, Polyvinyl alcohol, Povidone, Naphazoline Hydrochloride, or Glycerin.

Figures 2, 3:
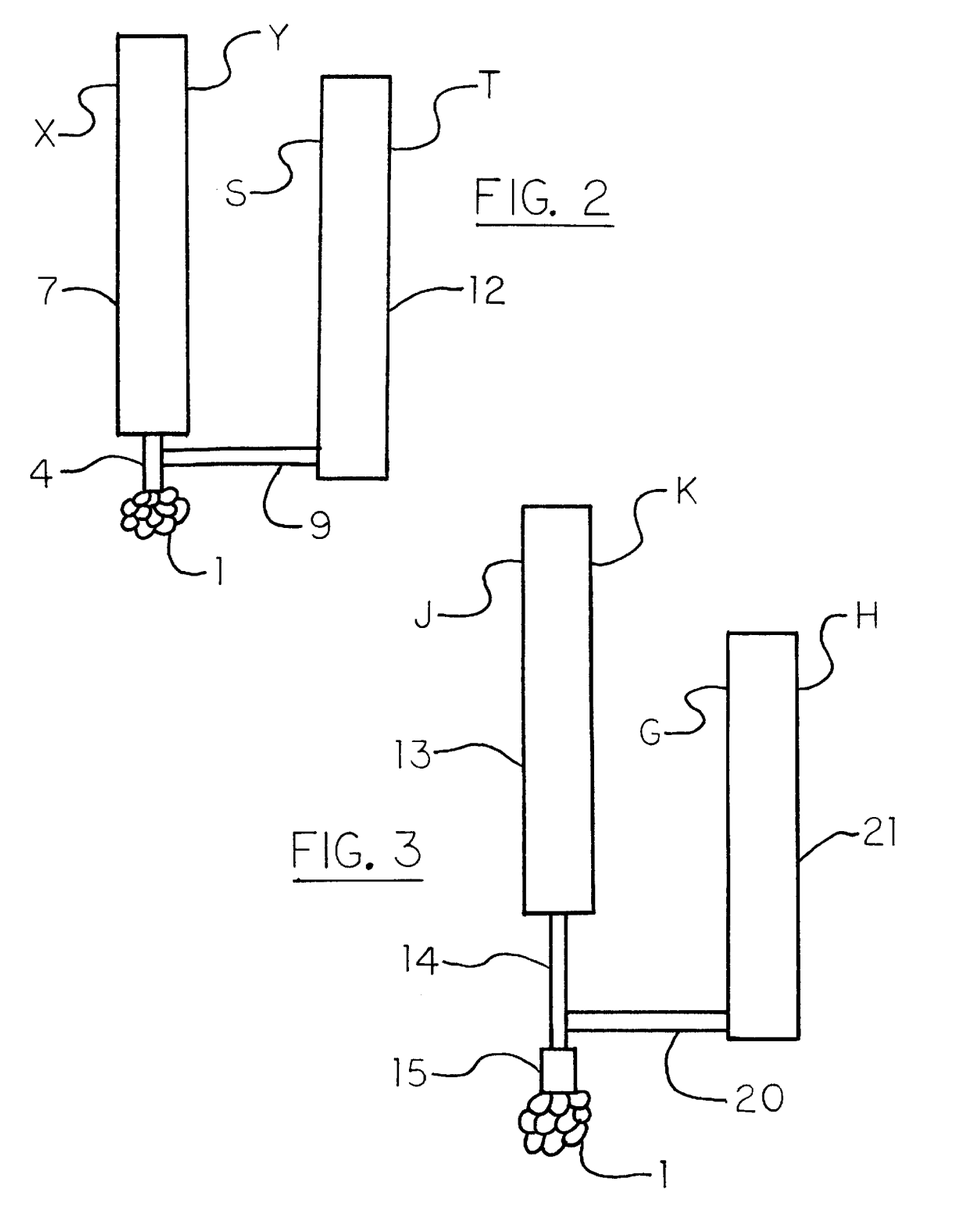
FIG. 2 is a frontal view of a first dispensing device.
FIG. 3 is a frontal view of a second dispensing device.
Figure 4:
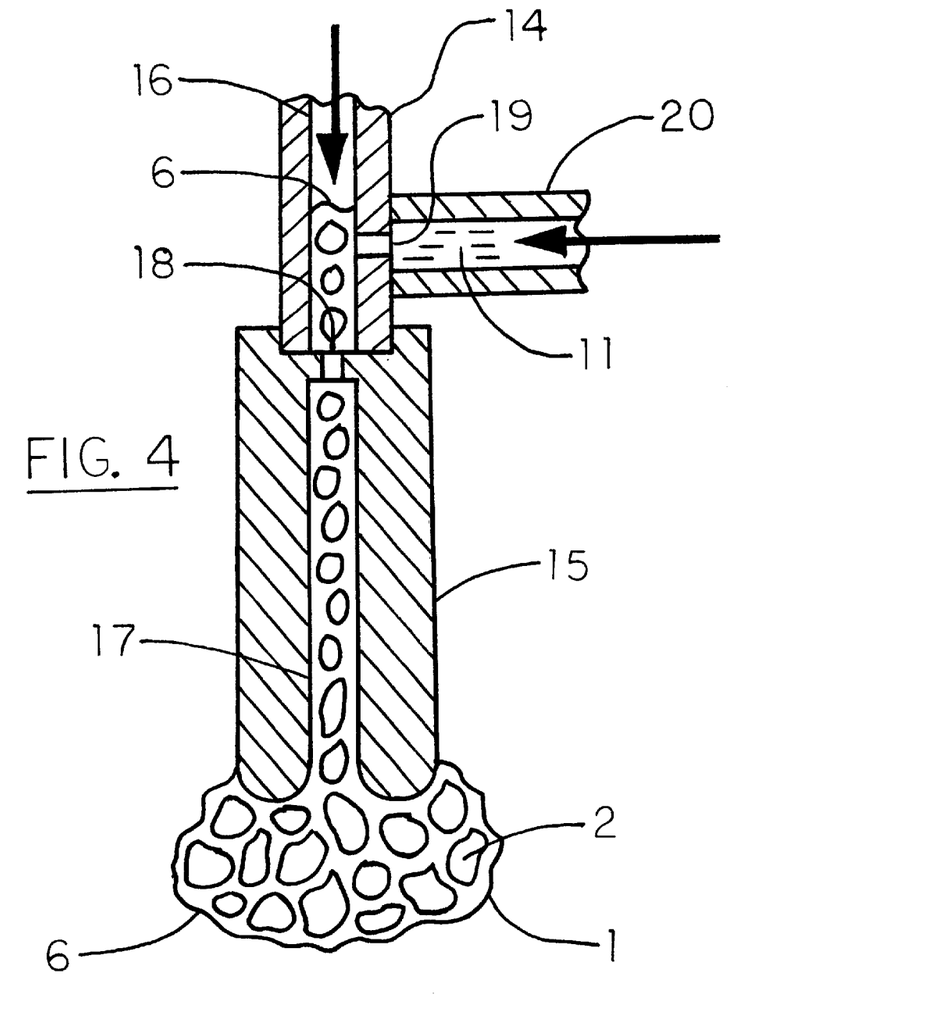
FIG. 4 is a frontal close-up sectional view of the gasdrop and a dispensing tip (15).

Referring to FIG. 1, and FIG. 2 there is shown, a FIRST DEVICE to form and dispense a Lg drop (1). A flexible plastic bottle (7) comprising, a tubular side wall, an integral upper disk shaped wall, and an integral lower disk shaped wall. The longitudinal axis of said tubular wall is disposed vertically. Said tubular wall, said upper wall, and said lower wall form a cylindrical shaped chamber having a uniform inner diameter of 10 millimeters, a length of 75 millimeters, and a volume of 6 cubic centimeters. Each said wall having a uniform thickness of 0.8 millimeters. Said upper wall may be fitted with a removeably attached leak tight cap, not shown, as there are many conventional methods. A centrally located opening (8) having a diameter of 0.3 millimeters is bored vertically through said lower wall.

A tube comprising, a dispensing tip (4) is attached to said lower wall. Dispensing tip (4) is co-axial with bottle (7), and disposed below thereof. An annular leak tight seal is formed at said attachment. The method of said and subsequent attachments and seals are not shown, as there are numerous conventional methods well known by those experienced in the art.

Dispensing tip (4) has a uniform inner diameter of 0.9 millimeters, a uniform wall thickness of 0.8 millimeters and an axial length of 9 millimeters. The inner diametrical surface of said dispensing tip forms a longitudinal flow channel (3) having an open lower end. Said flow channel comprises a substantially enclosed space. And said open lower end comprises an outlet. The lower extremity of said dispensing tip comprises an annular arcuate exterior surface, wherein the lowest extremity encompasses a circle lying in a horizontal plane. Bottle (7) communicates with the upper end of flow channel (3) via opening (8).

An opening (5) having a diameter of 0.5 millimeters, is bored horizontally through the tubular wall of dispensing tip (4). And opening (5) is disposed 3 millimeters below opening (8). A tube (9) is attached to the tubular wall of dispensing tip (4), such that tube (9) communicates with flow channel (3) via opening (5). An annular leak tight seal is formed at said attachment. Tube (9) extends laterally having a uniform inner diameter of 0.9 millimeters, a uniform wall thickness of 0.8 millimeters, and an overall length of 50 millimeters.

A flexible plastic bottle (12) comprising, a tubular side wall, an integral upper disk shaped wall, and an integral lower disk shaped wall. The longitudinal axis of said tubular wall is disposed vertically. Said tubular wall, said upper wall, and said lower wall form a cylindrical shaped chamber having a uniform inner diameter of 10 millimeters, a length of 75 millimeters, and a volume of 6 cubic centimeters. Each said wall having a uniform thickness of 0.8 millimeters. The free end of tube (9) penetrates through a lower wall of bottle (12). Thereby providing communication between flow channel (3) and bottle (12) via tube (9) and opening (5). An annular leak tight seal is formed at said penetration. The components of said first device, and the following devices, can be manufactured by numerous standard methods, such as injection molding, and or injection blow molding. And a typical material for the components is plastic.

As to make clear, said first device comprises,
Flexible bottle (7) communicates with the upper end of flow channel (3) via opening (8).
Flexible bottle (12) communicates with a medial portion of flow channel (3) via opening (5), and tube (9).
Flow channel (3) having an open lower end.

Referring to the above described first device, the following represents a method, among others, of use. 2 cubic centimeters of liquid (11) is placed in bottle (7). Bottle (12) contains air. Bottle (7) is held by a thumb at point "X" and a finger at point "Y". And bottle (12) is held by a thumb at point "S" and a finger at point "T". Points "X", "Y", "S", and "T" are respective opposing points on said tubular wall located near the upper end of said wall. The device is held such that the longitudinal axis of dispensing tip (4) is generally vertical, and the lowest extremity of dispensing tip (4) lies generally in a horizontal plane. It is preferred and beneficial to the formation of a Lg. drop to have a prone annular arcuate surface at said lowest extremity, however it is not required to be rounded, and numerous shapes are possible.

Bottle (7) and bottle (12) are concurrently compressed at an equal rate. Said collapsing is achieved by each said thumb and finger applying an opposing compressive force. The velocity of each wall during compression is approximately ten millimeters per second in a horizontal direction. Therefore, the amount of time required to collapse one bottle is approximately 500 milliseconds. And both bottles are concurrently collapsed within approximately 500 milliseconds. Said collapsing creates a pressure drop across opening (5) and opening (8). Thereby occurring collectively concurrent with said collapsing, comprising the steps of:

1.) Air (10) is injected into a medial portion of flow channel (3) via opening (5), in a direction shown by the horizontal arrow. Said injection having a predetermined input flow velocity, and a predetermined volumetric input flow rate.
2.) Liquid (11) is injected into the upper end of flow channel (3) via opening (8), in a direction shown by the vertical arrow. Said injection having a predetermined input flow speed, and a predetermined volumetric input flow rate.
3.) Said injections begin simultaneously at a predetermined location. Or if not simultaneously, begin injection of air (10) prior to beginning injection of liquid (11).
4.) Bubbles (2) are continually formed within the flow channel throughout the duration of said compression.
5.) Said continual formation induces a stream of integral contiguous bubbles (2) to flow downwardly thereof, exiting said flow channel through the lower open end, while remaining contiguous with subsequently formed bubbles.
6.) Said stream becomes inherently attached to the lower exterior surface of dispensing tip (4), thereby inducing an accumulation disposed below said exterior surface. Said attachment is due to the naturally occurring force of attraction between a liquid and a surface.

7.) Said accumulation comprises, one thin continuous liquid wall forming collectively, a bubble enclosing therein, a plurality of volumetrically similar bubbles, each enclosing therein, a gas.

8.) Upon obtaining a particular total mass; said accumulation becomes detached from said exterior surface. And said accumulation comprises a gasdrop.

Figures 6, 7:
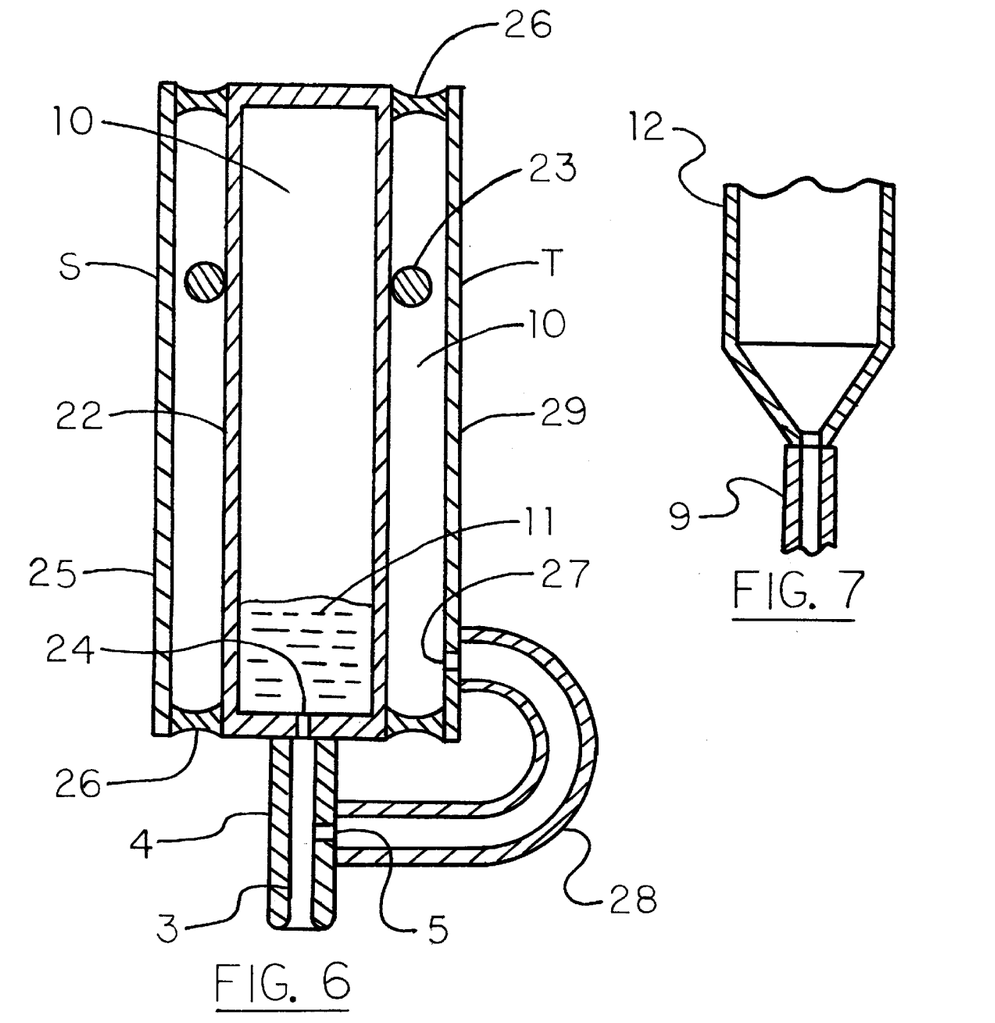
FIG. 6 is a frontal sectional view of a third dispensing device.
FIG. 7 is a frontal sectional view of a funnel configuration.

The above method is repeatable immediately after retraction of the bottle walls. Repeated use of this first device will likely induce an increasing accumulation of liquid (11) within bottle (12). This problem can easily be avoided by tapering the lower portion of the tubular wall, as shown in FIG. 7. Said tapering forms a funnel designed to have flowage from an upper large diameter to a lower small diameter. And any liquid within bottle (12) will accumulate at said small diameter. Said small diameter comprising the inner diameter of tube (9). Tube (9) is attached to bottle (12) such that said accumulation is disposed above the end of tube (9). This configuration comprises a chamber having one narrow outlet. And said configuration inhibits flowage into tube (9). The inhibiting of said flowage ensures the desired parameter of air (10) injected into the flow channel prior to the liquid. The combination of bottle (12) and tube (9) may be considered to be a reservoir for air (10). Upon each compression of the device, air will be injected into the flow channel via opening (5). Thereafter, said accumulation will be injected into the flow channel via tube (9). And upon retraction of the bottle walls, an accumulation returns. This process consistently repeats, thereby avoiding an increasing accumulation within bottle (12).

For example: There may be approximately 3 microliters of liquid (11) disposed at said small diameter after each retraction of the bottle walls.

Variations in the collapsing velocity are acceptable. However a slow collapsing velocity will likely dispense a solid drop. An example of said slow velocity is approximately 2 millimeters per second. As a result of said slow velocity, the bottles will be collapsed within approximately 2500 milliseconds. Typically, the characteristics of the gasdrop are relatively constant, within a range of collapsing velocities.

Variations in the dimensions of the device, may also produce variations of the gasdrop. And variations in several dimensions of the device will not produce variations of the gasdrop.

It is undesirable to begin collapsing bottle (7) before beginning to collapse bottle (12) whereas, this will likely dispense a solid drop. Therefore it is preferred to begin collapsing bottle (12) slightly before beginning to collapse bottle (7). This preferred sequence of collapsing causes air (10) to be injected into the flow channel prior to liquid (11) being injected. It is beneficial to continue injecting air into the flow channel after a sufficient quantity of liquid has been injected. And it is detrimental to continue injecting liquid into the flow channel, without injecting air.

Therefore it may be preferred to: a.) Slightly increase the inner diameter of bottle (12). b.) Slightly decrease the inner diameter of bottle (7). c.) Begin collapsing bottle (12) slightly before beginning to collapse bottle (7). d.) And continue collapsing bottle (12) whereas bottle (7) has stopped collapsing. While compressing each respective wall at an approximate velocity of 10 millimeters per second. The time required to collapse bottle (7) will be slightly less than 500 milliseconds.

For Example: The inner diameter of bottle (12) may be 14 millimeters, and the inner diameter of bottle (7) may be 7 millimeters.

The gasdrop will fall from dispensing tip (4) when the force due to gravity acting on said gasdrop is greater than or equal to the force of attraction between said gasdrop and dispensing tip (4).

For Example: The gasdrop is allowed to be formed upon a prone surface, and become detached from said surface by similar physical laws of nature that allow the well known solid eye drop to be formed and dispensed.

The overall size of the gasdrop is partially determined by the amount of surface area within a short vertical distance of the lowest extremity of dispensing tip (4). For example: Increasing said surface area, will likely dispense a larger Lg drop. This first device will typically produce a Bubble Drop with an overall outside dimension of approximately 6 millimeters. A constituent bubble (2), may have a diameter between approximately 0.5 millimeters and approximately 1 millimeter. Therefore a bubble (2) may enclose a volume between approximately 0.5 microliters and approximately 4 microliters.

Referring to FIG. 3, there is shown, a SECOND DEVICE to dispense a gasdrop. A flexible plastic bottle (13) comprising, a tubular side wall, an integral upper disk shaped wall, and an integral lower ring shaped wall. The longitudinal axis of said tubular wall is disposed vertically. Said tubular wall, said upper disk shaped wall, and said lower ring shaped wall form a cylindrical shaped chamber having a uniform inner diameter of 10 millimeters, a length of 75 millimeters and a volume of 6 cubic centimeters. Each said wall having a uniform thickness of 0.8 millimeters.

An upper end of a tube (14) is integrally formed with said lower ring shaped wall. And tube (14) is co-axial with bottle (13). Tube (14) extends downwardly from said lower wall a length 25 millimeters to a lower end. Tube (14) having a uniform inner diameter of 1 millimeter and a uniform wall thickness of 0.8 millimeters. The inner diametrical surface of tube (14) comprises a longitudinal flow channel (16). Bottle (13) communicates with flow channel (16).

A tube comprising, a dispensing tip (15) is attached to the lower end of tube (14). An annular leak tight seal is formed at said attachment. Said dispensing tip comprises a tubular side wall co-axial with tube (14) and disposed below thereof. The inner diametrical surface of said dispensing tip comprises a longitudinal flow channel (17). Said dispensing tip is also formed with an integral upper disk shaped wall, closing the upper end of flow channel (17). Said disk shaped wall also closes the lower end of flow channel (16). A centrally located opening (18) is bored vertically through said disk shaped wall. Said tubular wall, and said upper wall having a uniform thickness of 0.8 millimeters. The lower end of flow channel (17) is open to the exterior. The lower end of dispensing tip (15) is formed with an annular arcuate surface whereas, the lowest extremity of said surface encompasses a circle lying in a horizontal plane.

Opening (18) provides communication between flow channel (16) and flow channel (17). An opening (19) having a diameter of 0.3 millimeters is bored horizontally through the wall of tube (14). Opening (19) is disposed 3 millimeters from the lower end of tube (14). A tube (20) is attached to tube (14) such that tube (20) communicates with opening (19). An annular leak tight seal is formed at said attachment. Tube (20) extends laterally a length 25 millimeters, and having a uniform inner diameter of 0.9 millimeters.

A flexible plastic bottle (21) is comprised of a tubular side wall, an integral upper disk shaped wall, and an integral lower disk shaped wall. The longitudinal axis of said tubular wall is disposed vertically. Said tubular wall, said upper disk shaped wall, and said lower disk shaped wall form a cylindrical shaped chamber having a uniform inner diameter of 10 millimeters, a length of 75 millimeters and a volume of 6 cubic centimeters. Each said wall having a uniform thickness of 0.8 millimeters.

The free end of tube (20) penetrates through a lower wall of bottle (21) thereby providing communication between bottle (21) and flow channel (16). An annular leak tight seal is formed at said penetration. The upper disk shaped wall of bottle (21) may be fitted with a removable leak tight cap, not shown as there are many conventional methods.

As to make clear, said second device comprises, Bottle (13) communicates with flow channel (16). The lower end of flow channel (16) is closed by a wall.

Flow channel (17) is disposed below said wall.

The lower end of flow channel (16) communicates with the upper end of flow channel (17) via opening (18).

Flow channel (17) having a lower end thereof open to the exterior.

Bottle (21) communicates with the lower end of flow channel (16) via tube (20) and opening (19).

Referring to the above described second device, the following represents a method, among others, of use. 2 cubic centimeters of liquid (11) is placed in bottle (21). Bottle (13) contains air (10). Bottle (13) is held by a thumb at point "J" and a finger at point "K". Bottle (21) is held by a thumb at point "G" and a finger at point "H". Points "J", "K", "G", and "H" are respective opposing points on said tubular wall located near the upper end of said wall. The device is held such that the longitudinal axis of flow channel (17) is generally vertical. Bottle (13) and bottle (21) are concurrently compressed at an equal rate. Said collapsing is achieved by each said thumb and finger applying an opposing compressive force. The velocity of each wall, during compression, is approximately ten millimeters per second in a horizontal direction. Therefore, the amount of time required to collapse one bottle is approximately 500 milliseconds. And both bottles are concurrently collapsed within approximately 500 milliseconds. Thereby occurring collectively concurrent with said collapsing comprising the steps of:

1.) liquid (11) is injected into the lower end of flow channel (16) via opening (19), in a direction shown by the horizontal arrow. Said injection having a predetermined input flow speed, and a predetermined volumetric input flow rate.
2.) air (10) is injected into the lower end of flow channel (16), in a direction shown by the vertical arrow. Said injection having a predetermined input flow velocity, and a predetermined volumetric input flow rate.
3.) Said injections begin simultaneously at a predetermined location. Or if not simultaneously, begin injection of air (10) prior to beginning injection of liquid (11).
4.) integral contiguous bubbles are formed within the lower end of flow channel (16).
5.) Said bubbles, and a pressure drop across opening (18) induce a simultaneous injection of said liquid and said air into flow channel (17) via opening (18) thereby,
6.) inducing formation of contiguous bubbles within flow channel (17) thereby,
7.) inducing a stream of contiguous bubbles to flow through flow channel (17).
8.) Said stream exits flow channel (17) through the outlet thereof, becoming inherently attached to said outlet thereby,
9.) inducing an accumulation disposed below said outlet. Said inherent attachment is due to the naturally occurring force of attraction between a liquid and a surface.
10.) Said accumulation comprises, one thin continuous liquid wall forming collectively; a closed chamber enclosing therein, a plurality of volumetrically similar closed compartments, each enclosing therein, a gas.
11.) Upon obtaining a particular total mass; said accumulation becomes detached from said exterior surface. Said accumulation comprises a gasdrop.

The method described above is repeatable immediately after retraction of the bottle walls. This second device may also develop an increasing accumulation of liquid (11) within bottle (13) upon repeated use. And as previously mentioned, the bottle walls may be formed with a funnel portion to maintain a consistent accumulation.

Extreme variations in the collapsing velocity may be detrimental to the formation of the gasdrop. A slow collapsing velocity will likely dispense a solid drop. An example of said slow velocity is approximately 2 millimeters per second. Typically, the characteristics of the gasdrop are relatively constant with slight variations of the collapsing velocity. Variations in the dimensions of the device may also produce variations of the gasdrop. And variations in several dimensions of the device will not produce variations of the gasdrop.

It is undesirable to begin collapsing bottle (21) before beginning to collapsing bottle (13). Whereas, this will likely dispense a solid drop. Therefore it is preferred to inject air into flow channel (16) prior to injecting liquid. It is beneficial to continue injecting air into said flow channel after a sufficient quantity of liquid is injected. And it is detrimental to continue injecting liquid into said flow channel without injecting air.

Therefore it is preferred to: i.) Increase the inner diameter of bottle (13). ii.) Begin collapsing bottle (13) before beginning to collapse bottle (21). iii.) Continue collapsing bottle (13) whereas bottle (21) has stopped collapsing.

For Example: Bottle (13) may have an inner diameter of 17 millimeters, and bottle (21) may have an inner diameter of approximately 7 millimeters.

The first device, second device, and following third device are intentionally designed to be collapsed in a respective area of the bottle containing air. Referring to bottle (21), the particular change in air pressure within said bottle, due to collapsing said bottle, induces the appropriate volumetric input flow rate, and input flow speed. As it is known by those educated in the science, air is compressible, whereas a liquid is approximately not compressible. For example: If bottle (21) is completely filled with liquid, and collapsed as previously described, a detrimental quantity of liquid will be injected into the flow channel. This will likely dispense a solid drop.

The gasdrop shown in FIG. 3 will fall from dispensing tip (15) due to the physical laws of nature as previously described.

As shown in FIG. 3, the gasdrop accumulates on a surface having a lowest extremity. The overall size of the gasdrop is partially determined by the amount of surface area, within a short vertical distance of said lowest extremity.

The following example is given to clarify said term; "within a short vertical distance", and demonstrate a method to change the quantity of said surface area.

EXAMPLE

Given a discrete cylindrical shaped tube having a uniform inner diameter of 1 mm, a uniform wall thickness of 1 mm, and an axial length of 10 mm. Whereas the longitudinal axis of said tube is vertical, and a lower ring shaped surface lies in a horizontal plane. Said ring shaped surface comprises the lowest extremity, having an exterior surface area of 6.3 sq mm. The total exterior surface area within a vertical distance of 1.5 mm from said horizontal plane is 20.4 sq mm. The distance 1.5 mm represents a short vertical distance. A short vertical distance can also be approximately 3 mm.

The surface area (20.4 sq mm) can easily be altered. Rotate said tube 90 degrees about a horizontal axis. Said longitudinal axis is now horizontal and said ring shaped surface lies in a vertical plane. The lowest extremity of this tube is represented by a horizontal line having a length of 10 mm. And the total exterior surface area within a vertical distance of 1.5 mm from said line is 53.4 sq mm.

Various surface areas within a short vertical distance of the lowest extremity can easily be achieved by rotating said tube by any desired angle. The first device and second device are intended to have a lowest extremity disposed in a horizontal plane, however the present invention is not limited to theses devices and there are numerous possible shapes, quantities, and orientations of said surface area.

There are numerous possible variations of the first device, and the second device which will produce an acceptable gasdrop.

For example: The flow channel may have a cross section that is; square, triangular, or oval, and including others. The flow channel may have a conical shape, including others. Referring to openings (8), (19), and (24), said openings are not required to be a cylindrical shaped opening having a diameter of 0.3 millimeters. Said openings may be comprised of well known configurations used on typical non-pharmaceutical eye drop bottles. For example: A typical commercially available eye drop bottle, used for redness relief, comprises a flexible plastic bottle having a small outlet. Whereas said small outlet is designed to inhibit flowage from the bottle. And a pressure drop is required to dispense the liquid. Therefore opening (8), opening (19), or opening (24) may be comprised of a configuration similar to said small outlet.

A variation of said first device, comprising a THIRD DEVICE to dispense a gasdrop is shown in FIG. 6. This third device incorporates an alternate bottle configuration, thereby providing a preferred method of controlling the injection parameters.

The third device comprises, a flexible plastic bottle (22) having a tubular side wall, an upper disk shaped wall, and a lower disk shaped wall. The longitudinal axis of bottle (22) is disposed vertically. Said tubular wall, said upper wall, and said lower wall form a cylindrical shaped chamber having a uniform inner diameter of 7 millimeters, a length of 110 millimeters, and a volume of 4 cubic centimeters. Said tubular wall having a uniform thickness of 0.4 millimeters. Said upper wall and said lower wall having a uniform thickness of 0.8 millimeters. Said upper wall may be fitted with a removably attached leak tight cap, not shown as there are many conventional methods.

A rubber o-ring (23) having an inner diameter of 7.2 millimeters, an outer diameter of 11.8 millimeters, and a width of 2.3 millimeters, is placed on the exterior of said tubular wall. The inner diameter of the o-ring having an annular contact with said tubular wall, and disposed a uniform 33 millimeters from said upper wall. A centrally located opening (24) having a diameter of 0.3 millimeters is bored vertically through said lower wall.

The previously described dispensing tip (4) is attached to said lower wall such that flow channel (3) is co-axial with bottle (22) and disposed below thereof. Bottle (22) communicates with flow channel (3) via opening (24). An annular leak tight seal is formed at said attachment.

A flexible plastic tube (25) is disposed co-axial with and surrounds bottle (22). Tube (25) having a uniform inner diameter of 13 millimeters, an axial length of 110 millimeters, and a uniform wall thickness of 0.4 millimeters. An annular leak tight seal (26) is formed at each end of tube (25), thereby forming a flexible bottle (29) having a volume of 9 cubic centimeters.

An opening (27) having a diameter of 0.8 millimeters is bored horizontally through the lower end of tube (25). A tube (28) is attached thereof such that tube (28) communicates with opening (27). An annular leak tight seal is formed at said attachment. Tube (28) having a uniform inner diameter of 0.8 millimeters, and a length of 40 millimeters. The free end of tube (28) is attached to dispensing tip (4) such that tube (28) communicates with opening (5). An annular leak tight seal is formed at said attachment.

As to make clear, the third device comprises:
Bottle (22) co-axial with, and surrounded by bottle (29).
Bottle (22) having an attached o-ring (23).
Bottle (22) communicates with flow channel (3) via opening (24).
Bottle (29) communicates with flow channel (3) via opening (27), tube (28), and opening (5).

Referring to the above described third device, the following represents a method, among others, of use. One cubic centimeter of liquid (11) is placed in bottle (22). The use of this third device, and the bubble forming process, is similar to previously described methods. The device is held by a thumb at point "S" and a finger at point "T". Whereas said points are opposing points on the tubular wall of bottle (29), and located near o-ring (23). Opposing compressive forces are applied to bottle (29) by said thumb and finger thereby compressing bottle (29) at a constant rate. Bottle (22) is obviously collapsed as a result of tube (25) contacting o-ring (23). The walls of tube (25) collapse horizontally at approximately 10 millimeters per second. Therefore bottle (22) is collapsed within approximately 350 milliseconds.

This third device will typically dispense a gasdrop having an overall outside dimension of approximately 6 millimeters. And said gasdrop will be comprised of numerous volumetrically similar bubbles. Whereas said volume may be between approximately 0.5 microliters and approximately 4 microliters. And for example: a majority of said constituent bubbles may have a volume of approximately 4 microliters. Said gasdrop will have a generally spheroid shape. As previously stated, the size of the gasdrop can be altered by selection of a quantity of surface area. Said funnel shaped wall may also be incorporated.

This third device provides a method to inject air (10) into the flow channel prior to the liquid being injected. And also provides a method of stopping injections nearly simultaneously. The relative flexibility of tube (25) to the tubular wall of bottle (22), can be selected as a function of injection timing and injection rate. For example: If the tubular wall of bottle (22) has a uniform thickness of 0.3 millimeters. And tube (25) has a uniform thickness of 1.2 millimeters; Bottle (22) will collapse significantly before bottle (29) collapses. Therefore, by selection of various materials, and wall thickness, numerous variations of the device are possible. This co-axial bottle design may also be employed with the second device.

There is a limited quantity of surface area near point "S", and point "T" allowed to be compressed. Said area is limited to a axial dimension of approximately 25 millimeters, and includes a transverse dimension equal to the circumference of tube (25). For example, the width of a thumb may be approximately 25 millimeters. The shape of said tubular wall, upon collapsing, will typically conform to the approximate shape of the surface area applying compressive force. Whereas said shape can be used to determine the change in volume of each respective bottle. This change in volume is directly related to the change in pressure within each respective bottle. Said limited surface area also applies to the first device, and second device. It is possible for said limited surface area to vary in quantity, knowing there are other parameters to be considered with respect to such a change.

The gasdrop may also be formed upon alternate surface areas. It is possible for a stream of bubbles to flow upon a supine hemispherical surface, and accumulate thereupon. An example of said surface is a bowl. Upon obtaining a particular size, the device can be inverted, thereby dispensing the gasdrop.

Liquid (11) may have various input flow speeds and various volumetric input flow rates. As it is known, the gasdrop may not be required to meet a particular specification. Therefore, with respect to said liquid, it is possible to determine an acceptable range of input flow speeds. And it is possible to determine an acceptable range of volumetric input flow rates. Said ranges may be determined experimentally, or theoretically.

Air (10) may have various input flow velocities, and various volumetric input flow rates. Therefore it is possible to determine an acceptable respective range of said rates. Each said range may be determined experimentally, or theoretically.

The acceptable locations of said injections may be determined experimentally, or theoretically.

The term "input flow velocity" herein refers to the speed and direction of flow, immediately prior to entering the flow channel.

For Example: The input flow direction of air (10) in FIG. 1 is horizontal. And said speed can be measured in centimeters per second. The term "volumetric input flow rate" herein refers to the quantitative rate of flow immediately prior to entering the flow channel.

For Example: Said rate can be measured in cubic centimeters per second. The term "input flow speed" herein refers to the speed of flow immediately prior to entering the flow channel. And said speed can be measured in centimeters per second. The aforementioned methods of use induce particular input flow speeds, input flow velocities, and volumetric input flow rates, wherein each are processes related to fluid dynamics. And the laws of Physics in the field of Fluid Dynamics are well established and well know by those educated in the science. As it is known, an eye drop liquid may be comprised of different chemical elements. And the flowability of a particular liquid depends partially on the particular chemical composition. Therefore, given a particular liquid, and the specifications described herein, automated calculations of a range, or particular speed, velocity, or volumetric rate, can easily be determined.

Injection of gases and liquids into an enclosed space is a process well known by those experienced in the art. And there are numerous machines, and various methods to induce said injections.

For Example: Injection molding of plastic parts. These automated methods are not necessarily a preferred method, however they are provided to demonstrate the invention is not limited to the methods of injection described herein.

It is possible, a chemical reaction enhances the formation of bubbles formed within the flow channel. Injecting air into a compound may aerate said compound. And in consideration that chemistry is well known by those educated in the science. If a chemical reaction contributes to the formation said bubbles. Whereas given a particular liquid and the parameters described herein, said reaction can be easily determined. Liquid (11) is required to have bubble forming characteristics. Therefore, said characteristics may be enhanced by a chemical reaction induced by a bubble forming process described herein. And particularly, said chemical reaction may be aeration.

There have been three devices described to dispense a gasdrop. And while holding a device above and opposing the eye, said gasdrop can be easily dispensed upon a supine eye. Upon contact with the eye, the gasdrop will spread laterally over the surface of the eye, and constituent bubbles will burst upon contact with the eye. It is obvious random bursting may occur, however the structure of a gasdrop is very stable as compared to a single isolated bubble.

Figure 5:
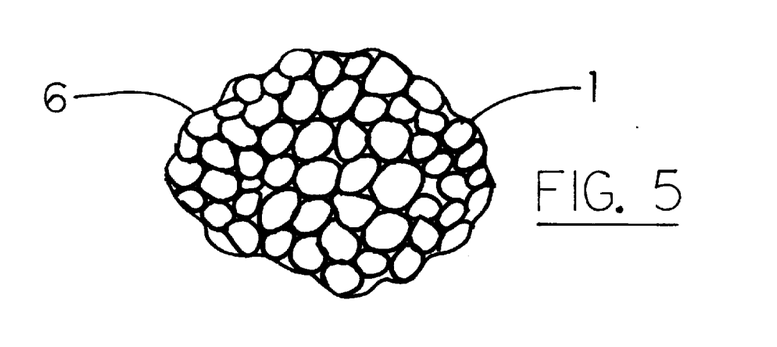
FIG. 5 is a frontal close-up view of the gasdrop.

Referring to FIG. 5, there is shown a frontal view of the gasdrop (1). Said Bubble Drop is generally symmetrical therefore FIG. 5 may also represent a side view or a top view. The exterior surface of the gasdrop comprises a spheroid shape.

As shown in the sectional view, FIG. 1, and while numerous cross-sectional views of the gasdrop are similar to FIG. 1, The gasdrop (1) comprises, one thin continuous liquid wall (6) forming collectively: 1.) A closed chamber enclosing therein, 2.) a plurality of volumetrically similar closed compartments (2). Each said compartment enclosing therein, a gas (10).

Wall (6) having an exterior, spheroid shaped portion, thereby forming said closed chamber. Particularly, said spheroid shaped portion comprises a large bubble. And as previously stated, said large bubble encloses therein, said plurality. Particularly, a said compartment comprises a small bubble. Therefore the gasdrop may particularly comprise, one thin continuous liquid wall forming collectively, a large bubble enclosing therein, a plurality of volumetrically similar small bubbles. And each said small bubble enclosing therein, a gas. For example: a majority of said constituent small bubbles may contain approximately 4 microliters of a gas.

Said spheroid shaped portion of wall (6) remains continuous and integrally formed with the interior portion of wall (6) during said bursting. And as a result of said bursting, the total surface area of wall (6) decreases. If a small bubble bursts within said chamber, the air released from this bubble will be contained within said chamber. This entrapment of air also contributes to the liquid remaining within a particular area during and after bursting. This ability of the liquid to remain within a particular area contributes to an improvement comprising, a reduced quantity of liquid spreading to undesired portions of the facial area.

The gasdrop allows the liquid to contact the eye at a reduced rate as compared to solid drops. And said reduced rate contributes to the improvement comprising, a gentle application of liquid to the eye.

If a gasdrop and a solid drop are comprised of an equal total mass. Said gasdrop will be substantially larger than said solid drop. And it is a well known physical law of nature thereof, distributing a particular force over a larger surface area, reduces the force per square unit of area. Therefore if said gasdrop and said solid drop fall upon an eye with equal velocities, said gasdrop will impact the eye with less force per square unit of area as compared to said solid drop. Said less force contributes to the feeling of a gentle application. This ability of the gasdrop to impact with less force contributes to the improvement comprising, a feeling of gentle application.

Obviously, many modifications and variations of the present invention, as hereinbefore set forth, may be made without departing from the spirit and scope thereof, and therefore, only such limitations should be imposed as are indicated by the appended claims.

I claim:

1. A method of manufacturing a gasdrop comprising the steps of:
   (i) beginning injection of a gas into a chamber, wherein said beginning injection of said gas goes into a predetermined substantially enclosed space having an outlet and said gas injection is within a predetermined range of input flow velocities, and within a predetermined range of volumetric input flow rates;
   (ii) beginning injection of a liquid into said chamber, wherein said liquid injection is within a predetermined range of input flow speeds, and within a predetermined range of volumetric input flow rates, and both said injection occurring at a predetermined location, and further wherein said liquid injection does not begin prior to said gas injection and concurrent with said injections;
   (a) manufacturing a stream of contiguous bubbles within said chamber, wherein said stream exits via said outlet;
   (b) inducing an accumulation of said bubbles, wherein said accumulation is contiguous with said outlet; and
   (c) inducing detachment of said accumulation wherein, said inducement consists essentially of gravitational force.

* * * * *